United States Patent
Cui et al.

(10) Patent No.: US 10,161,796 B1
(45) Date of Patent: Dec. 25, 2018

(54) LED LIGHTING BASED MULTISPECTRAL IMAGING SYSTEM FOR COLOR MEASUREMENT

(71) Applicant: Wenzhou University, Wenzhou (CN)

(72) Inventors: Guihua Cui, Wenzhou (CN); Xiukai Ruan, Wenzhou (CN); Qibo Cai, Wenzhou (CN); Yanhua Tan, Wenzhou (CN); Wenbin Xie, Wenzhou (CN); Jinjin Chu, Wenzhou (CN); Yaowu Liu, Wenzhou (CN); Ting Xu, Wenzhou (CN); Yaoju Zhang, Wenzhou (CN); Haiyong Zhu, Wenzhou (CN); Yuxing Dai, Wenzhou (CN)

(73) Assignee: Wenzhou University, Wenzhou (CN)

( * ) Notice: Subject to any disclaimer, the term of this patent is extended or adjusted under 35 U.S.C. 154(b) by 0 days.

(21) Appl. No.: 16/015,321

(22) Filed: Jun. 22, 2018

(30) Foreign Application Priority Data

Jun. 22, 2017 (CN) .......................... 2017 1 0481070

(51) Int. Cl.
*G01J 3/28* (2006.01)
*H04N 5/235* (2006.01)
*H05B 33/08* (2006.01)
*G01J 3/50* (2006.01)

(52) U.S. Cl.
CPC ............. *G01J 3/2823* (2013.01); *G01J 3/501* (2013.01); *H04N 5/2354* (2013.01); *H05B 33/0857* (2013.01)

(58) Field of Classification Search
CPC ........ G01J 3/28; G01J 3/02; G01J 3/50; G01J 3/00; H04N 5/235; H04N 5/358; H04N 5/374; H04N 5/378; H05B 33/08; G06F 3/04
See application file for complete search history.

(56) References Cited

U.S. PATENT DOCUMENTS

2012/0026512 A1* 2/2012 Schwarz .............. G01N 21/474
356/612

\* cited by examiner

*Primary Examiner* — Abdullahi Nur
(74) *Attorney, Agent, or Firm* — Wood Herron & Evans LLP

(57) ABSTRACT

An LED lighting based multispectral imaging system for color measurement is provided, including a main control computer and an enclosed type lamp box, where a digital camera is provided at the top of the lamp box, and an LED lamp set control apparatus, a drawer type bearing platform, and an LED lamp set are provided at the bottom of the lamp box. A to-be-measured object is placed on the drawer type bearing platform. The main control computer controls spectral power distribution of the LED lamp set to be in a reciprocal relationship with a spectral sensitivity curve of the digital camera and extracts a camera response and performs calculation, to obtain spectral reflectivity of each pixel of the to-be-measured object.

8 Claims, 1 Drawing Sheet

LED LIGHTING BASED MULTISPECTRAL IMAGING SYSTEM FOR COLOR MEASUREMENT

CROSS-REFERENCE TO RELATED APPLICATION

This application claims priority to Chinese application number 201710481070.7, filed on 22 Jun. 2017, with a title of LED LIGHTING BASED MULTISPECTRAL IMAGING SYSTEM FOR COLOR MEASUREMENT. The above-mentioned patent application is incorporated herein by reference in its entirety.

TECHNICAL FIELD

The present invention relates to the field of color measurement technologies.

BACKGROUND

Spectral reflectivity of an object is an important optical characteristic of an object surface and is also a "fingerprint" or "root cause" of a color of the object surface. Therefore, color measurement is an indispensable main means for controlling color reproduction quality in the color reproduction-related industry.

Conventional color measurement methods of an object surface include three methods: a visual method, a photoelectric integration method, and a spectrophotometric method. The details are as follows: (1) In the visual method, a standard colorimetric observer performs visual discrimination on a product in a particular lighting condition, and makes a comparison with a Commission International de l'Eclairage (CIE) standard chromaticity diagram or other standard color cards to obtain a color parameter; (2) In the photoelectric integration method, a typical instrument is a colorimeter, including four parts: a light source, a detector, a data processor, and an output unit. The detector is generally a color sensor, such as three phototubes each having a correction filter set or a silicon photoelectric diode with a large area. The method cannot accurately measure tristimulus values or chromaticity coordinates of an object, cannot provide spectral reflectivity of the object, but can accurately measure a color difference between two objects. Therefore, the colorimeter is also referred to as a color difference meter, and cannot be used for accurate color reproduction; (3) In the spectrophotometric method, an integrating sphere spectrophotometer is usually used to make a to-be-measured object illuminated evenly; and grating splitting is used to obtain monochromatic light, and tristimulus values of a color are further calculated by measuring spectral reflectivity of reflected (scattered) light of an opaque object or spectral transmittance of a transparent object, so as to obtain various color parameters. The method is used to determine color parameters of a to-be-detected sample by detecting spectral components of the to-be-detected sample, and therefore has quite high precision. Therefore, the method is applicable to measurement of reflectivity of an object surface or transmittance of a transparent material during most color measurement.

The inventor found that the foregoing three conventional color measurement methods all have disadvantages. The disadvantages lie in that: The visual method is highly correlated with individual psychology and physiology of an observer, the measurement has strong subjectivity, low precision, and complex operations, and there is a relatively large difference between different observers; while the photoelectric integration method and the spectrophotometric method both are a contact measurement method, that is, a measuring aperture of an instrument needs to be tightly attached to a surface of a to-be-measured object, to prevent external light from entering the measurement instrument; and therefore, a primary characteristic of a surface of a fragile object is easily damaged, a fragile valuable high-temperature high-humidity object cannot be measured, and an article that possibly pollutes or damages the instrument, such as food, oil paint, and printing ink, also cannot be measured. A most criticized limitation of conventional color measurement methods is that: Only a target object with a specific size can be measured, and an object color of a tiny object, for example, a single pixel in an image, cannot be measured; and fine color reproduction for cultural relics, biomedicine, 3D printing, and the like cannot be implemented. All these are key technical problems that need to be resolved in current color detection methods.

Therefore, a color measurement method is needed to overcome the limitations of existing color measurement instruments, measure a color of a tiny object such as a pixel on an object surface in a non-contact manner, and for use in fields in which the conventional color measurement instruments cannot be applied, such as measurement of food and beverage, liquid, cosmetics, an object with a rough and uneven surface and an irregular shape, and the like.

SUMMARY

An object of the present invention is to provide an LED lighting based multispectral imaging system for color measurement to overcome disadvantages in the prior art, so as to avoid undesirable limitations of conventional color measurement methods in a non-contact manner. The system of this invention can be used in fields in which conventional color measurement instruments cannot be applied.

To resolve the above technical problem, embodiments of the present invention provide an LED lighting based multispectral imaging system for color measurement, including a main control computer and an enclosed type lamp box for placing a to-be-measured object. A digital camera is provided at the top of the lamp box, an LED lamp set control apparatus is provided in central enclosed space at the bottom of the lamp box, a drawer type bearing platform that is used for placing the to-be-measured object and that enters or exits from the lamp box through an external drive is provided in an upper part of the lamp box, and at least one LED lamp set is provided on each of two sides at the bottom of the lamp box. The digital camera aims at the to-be-measured object and is connected to the main control computer and is configured to shoot an image of the to-be-measured object. Each LED lamp set includes a plurality of monochromatic LED lamps with different peak wavelengths. The LED lamp set control apparatus is connected to each LED lamp set and the main control computer and is configured to receive a control instruction sent by the main control computer and control turn-on or turn-off and an illumination degree/illumination degrees of one or more LED lamps of the LED lamp set according to the received control instruction. The main control computer is configured to control, according to a spectral sensitivity curve of the digital camera, spectral power distribution of each LED lamp set to be in a reciprocal relationship with the spectral sensitivity curve of the digital camera, output the control instruction to drive the LED lamp set control apparatus to turn on a corresponding LED lamp in each LED lamp set, receive an image, of the to-bemeasured object, that is shot by the digital camera when the corresponding LED lamp in the LED lamp set is turned on, and extract a camera response and perform calculation, to obtain spectral reflectivity of each pixel of the to-be-measured object.

In one aspect, all monochromatic LED lamps included in any LED lamp set are cross arranged on an LED circuit board provided with an LED lamp bead array, the LED circuit board is fastened onto a radiating fin, and a light scattering sheet is provided at a specific distance from one side of a luminous surface of the LED circuit board.

In another aspect, any LED lamp set is fastened onto two sides at the bottom of the lamp box and forms a specific acute angle with a plane of the bottom of the lamp box; and the luminous surface of LED lamp set tilts towards one of inner walls on two sides of the lamp box.

In a further aspect, there are at least two LED lamp sets having an exactly same structure, and the LED lamp sets are provided opposite to each other on two sides of the to-be-measured object.

In some aspects, the digital camera is a high-speed black-and-white camera or a high-speed color camera.

Compared with the prior art as described in some detail above, the advantages and beneficial effects of the present invention are as follows: 1. In the present invention, a main control computer controls an LED lamp set including a plurality of monochromatic LED lamps with different peak wavelengths to simulate an active lighting source whose spectral sensitivity curve is in a reciprocal relationship with that of a digital camera, to illuminate a to-be-measured object, and sequentially obtains multispectral images of the to-be-measured object that are acquired by the digital camera; extracts color information of a surface of the to-be-measured object from the multispectral images; and reconstructs spectral reflectivity of the surface of the to-be-measured object, to measure a color of the to-be-measured object. The method has advantages, such as a simple algorithm, a small system error, high measurement accuracy, and can break through limitations of conventional color measurement methods. Non-contact color measurement can be used in fields in which conventional color measurement instruments cannot be applied. 2. In the present invention, an LED lamp is used as an active lighting source to construct a multispectral imaging system, so as to avoid use of an optical splitting system, reduce system costs, and increase a multispectral image acquisition speed.

BRIEF DESCRIPTION OF THE DRAWINGS

Various additional features and advantages of the invention will become more apparent to those of ordinary skill in the art upon review of the following detailed description of one or more illustrative embodiments taken in conjunction with the accompanying drawings. The accompanying drawings, which are incorporated in and constitute a part of this specification, illustrates one or more embodiments of the invention and, together with the general description given above and the detailed description given below, explains the one or more embodiments of the invention.

DETAILED DESCRIPTION

Embodiments of the invention are illustrated below with reference to the accompanying drawings. The preferred embodiments described here are used only to describe and explain the present disclosure, but not to limit the present disclosure.

Figure 1:
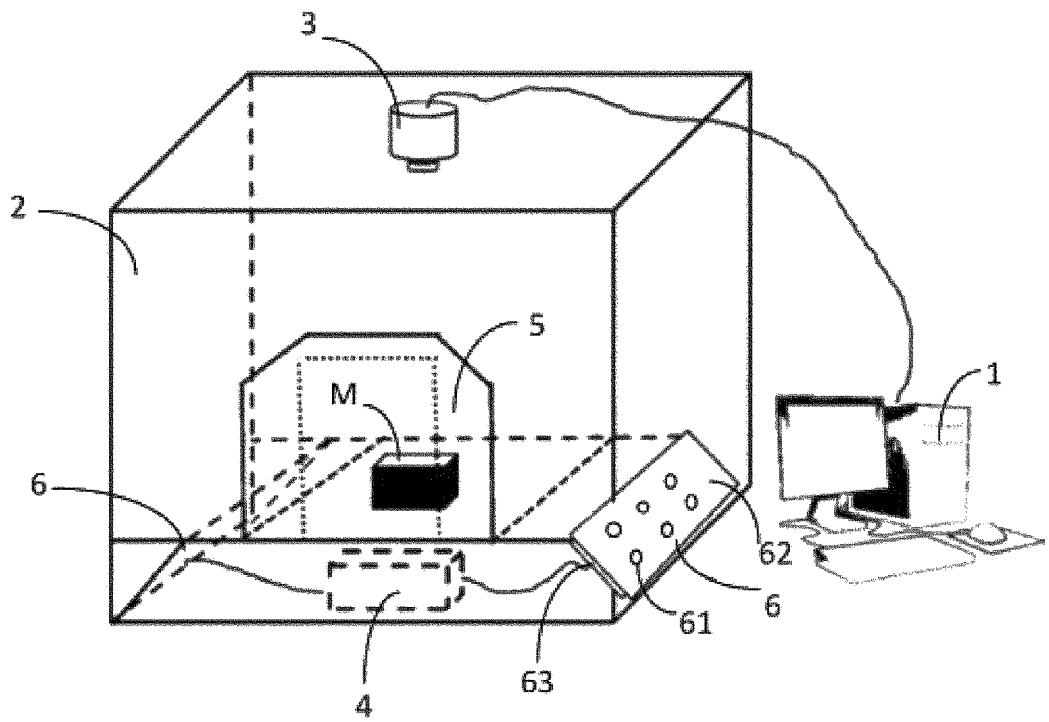
FIG. 1 is a schematic structural diagram of an LED lighting based multispectral imaging system for color measurement according to one embodiment of the present invention.

FIG. 1 shows an LED lighting based multispectral imaging system for color measurement according to an embodiment of the present invention. The multispectral imaging system includes a main control computer 1 and an enclosed type lamp box 2 for placing a to-be-measured object M.

A digital camera 3 is provided at the top of the lamp box 2, an LED lamp set control apparatus 4 is provided in central enclosed space at the bottom of the lamp box 2, a drawer type bearing platform 5 that is used for placing the to-be-measured object M and that enters or exits from the lamp box 2 through an external drive is provided in an upper part of the lamp box 2, and at least one LED lamp set 6 is provided on each of two sides at the bottom of the lamp box 2. The digital camera 3 aims at the to-be-measured object M and is connected to the main control computer 1 and is configured to shoot an image of the to-be-measured object M. Each LED lamp set 6 includes a plurality of monochromatic LED lamps with different peak wavelengths. The LED lamp set control apparatus 4 is connected to each LED lamp set 6 and the main control computer 1 and is configured to receive a control instruction sent by the main control computer 1 and control turn-on or turn-off and an illumination degree/illumination degrees of one or more LED lamps of the LED lamp set according to the received control instruction.

The main control computer 1 is configured to control, according to a spectral sensitivity curve of the digital camera 3, luminescent spectrum power distribution of each LED lamp set 6 to be in a reciprocal relationship with the spectral sensitivity curve of the digital camera 3, output the control instruction to drive the LED lamp set control apparatus 4 to turn on a corresponding LED lamp in each LED lamp set 6 and adjust brightness of the corresponding LED lamp, receive an image of the to-be-measured object that is captured by the digital camera 3 when the corresponding LED lamp in the LED lamp set 6 is turned on, and extract a camera response and perform calculation, to obtain spectral reflectivity of each pixel of the to-be-measured object M.

It should be noted that an opening is provided in the lamp box 2, so that the drawer type bearing platform 5 can enter or exit from the lamp box 2 through the external drive; and after the drawer type bearing platform 5 entirely enters the lamp box 2, the whole lamp box is also an enclosed structure. In addition, to reduce installation space and avoid interference on a light source, the LED lamp set control apparatus 4 may be located in enclosed space below the drawer type bearing platform 5 and is connected to the main control computer 1 in a wired or wireless manner. The digital camera 3 may be a high-speed black-and-white camera or a high-speed color camera, and the spectral sensitivity curve corresponding to the digital camera 3 may be obtained by using an image, captured in a natural light condition, of a standard color card, may be pre-stored in the main control computer 1.

It should be noted that, to fully evenly illuminate the to-be-measured object M, a quantity of LED lamp sets 6 may be appropriately increased, the LED lamp sets 6 are symmetrically placed on the two sides at the bottom of the lamp box 2, and luminous surfaces of all LED lamp sets 6 tilt towards one of inner walls on two sides of the lamp box 2; and the to-be-measured object M is illuminated through light reflection and scattering on the inner wall.

In this embodiment of the present invention, a working principle of the LED lighting based multispectral imaging system for color measurement is as follows. The main control computer 1 controls the LED lamp set 6 including a plurality of monochromatic LED lamps with different peak wavelengths to simulate an active lighting source whose spectral sensitivity curve is in a reciprocal relationship with that of the digital camera 3, to illuminate the to-be-measured object M; sequentially obtains multispectral images of the to-be-measured object M that are acquired by the digital camera 3 when the LED lamps perform illumination; extracts color information of a surface of the to-be-measured object M from the multispectral images; and reconstructs spectral reflectivity of the surface of the to-be-measured object M, to measure a color of the to-be-measured object M. Therefore, in this embodiment of the present invention, the LED lighting based multispectral imaging system for color measurement has advantages, such as a simple algorithm, a small system error, high measurement accuracy, and thereby overcomes limitations of conventional color measurement methods. A non-contact color measurement method can be used in fields in which conventional color measurement instruments cannot be applied.

Further, all the LED lamp sets 6 have an exactly same structure, all monochromatic LED lamps included in the LED lamp set 6 are cross arranged on an LED circuit board 62 provided with an LED lamp bead array 61, and a light scattering sheet 63 is provided on one side of a luminous surface of the LED circuit board 62. In addition, all the LED lamp sets 6 are fastened onto two sides at the bottom of the lamp box 2, and each LED lamp set 6 forms a specific acute angle with a plane of the bottom of the lamp box 2; and the luminous surface tilts towards one of the inner walls on the two sides of the lamp box 2. This facilitates illumination of the to-be-measured object M.

Figure 2:
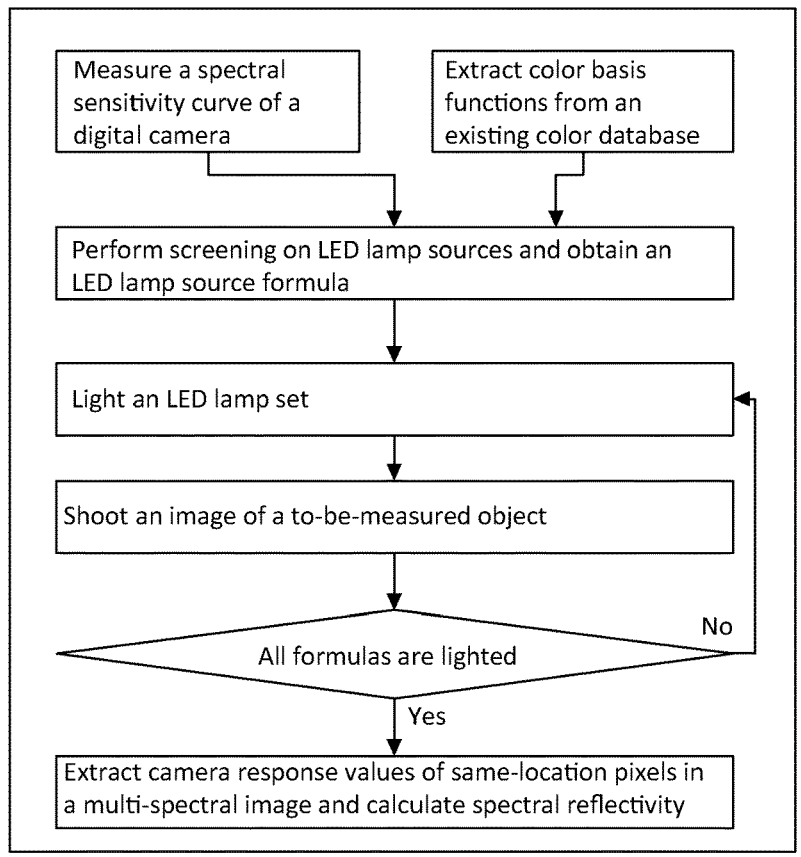
FIG. 2 is a flowchart of an implementation method of an LED lighting based multispectral imaging system for color measurement according to another embodiment of the present invention.

FIG. 2 shows a specific implementation method of an LED lighting based multispectral imaging system for color measurement according to an embodiment of the present invention. Details are as follow:

Step 1. Measure a spectral sensitivity curve of a digital camera, where the spectral sensitivity curve $s(\lambda)$ of the digital camera may be measured by using two rapid and accurate methods for measuring a spectral sensitivity curve. A first method is a monochrometer measurement method in which an image of a standard white plate is shot at different sampling wavelengths $\lambda$ and spectral power distribution of monochromatic light is measured at the different sampling wavelengths $\lambda$, and spectral sensitivity is obtained through calculation. The method has a relatively long experimental process, but has relatively small calculation amount and simple calculation. A second method is a camera imaging method in which the digital camera shoots an image of a standard color card in a natural light condition, measures relative spectral power distribution of a nature light source and spectral reflectivity of each color block in the standard color card, and obtains spectral sensitivity by using an optimization method. The method is suitable for real-time spectral sensitivity measurement.

Step 2. Extract color basis functions, where m (usually, 5 to 8) color basis functions are extracted from an existing color database, such as spectral reflectivity of a Munsell color card, and linear combination of the m color basis functions indicates object reflectivity $r(\lambda)$, that is, $$r(\lambda) = \sum_{i=1}^{m} \sigma_i b_i(\lambda) \quad (1)$$

where $b_i(\lambda)$ is an orthogonal basis function, determined through statistics collection, of the object reflectivity, $\sigma_i$ is a set of weight factor, and $\lambda$ is an optical wavelength. When basis functions are known, for different object surfaces, spectral reflectivity of the object surfaces can be reconstructed as long as weight factors of the basis functions are determined.

Step 3. Perform screening on LED lamp sources and obtain an LED lamp source formula, where relative spectral power distribution of an $i^{th}$ light source is set to $l_i(\lambda)=b_i(\lambda)/s(\lambda)$, namely, a ratio of an $i^{th}$ basis function $b_i(\lambda)$ to sensitivity $s(\lambda)$ of a sensor of the camera, corresponding camera output $O(ti)$ at a moment $t_i$ is a weight factor of a corresponding basis function $\sigma_i=O(t_i)$ and is substituted into Formula (1), and spectral reflectivity can be reconstructed from m camera output signals:

$$r(\lambda) = \sum_{i=1}^{m} k_i O(t_i) b_i(\lambda) \quad (2)$$

where $k_i$ indicates a camera response scaling factor corresponding to the $i^{th}$ light source, and is related to illumination intensity of the light source and camera exposure. When the camera exposure is fixed, $k_i$ can be obtained through optimization by using a multispectral image of the standard color card with known spectral reflectivity.

An appropriate monochromatic LED lamp with different peak wavelengths is selected to perform precise fitting to obtain a required light source spectrum. Because existing available LED lamps are limited, an LED lamp bead needs to be preferably selected according to the required light source spectrum, the LED lamp source formula is obtained by using a curve fitting method, and a drive current of each LED lamp is calculated when light sources meeting different requirements are used. Step 4. Light an LED lamp set, where a PWM (pulse width modulation) technology is used to design a control mode of an LED lamp set control apparatus, to make brightness control bit depth of each LED lamp not less than 1024, so as to accurately simulate spectral power distribution of a required light source.

Step 5. Shoot an image of a to-be-measured object, where when a corresponding LED lamp is controlled to be turned on, images of the to-be-measured object are sequentially shot through control of exposure parameters of the digital camera when m light sources are used, and are transmitted to a main control computer.

Step 6. Extract camera response values of same-location pixels in a multi-spectral image and calculate spectral reflectivity, where camera response values $O(t_i)$ of same-location pixels in m multi-spectral images are extracted, where i=1 . . . m; the camera response values $O(t_i)$, the corresponding basis function $b_i(\lambda)$ and $k_i$ values are substituted into Formula (2) to obtain spectral reflectivity of each pixel of the to-be-measured object.

Compared with the prior art, the advantages and beneficial effects of the present invention are: 1. In the present invention, a main control computer controls an LED lamp set including a plurality of monochromatic LED lamps with different peak wavelengths to simulate an active lighting source whose spectral sensitivity curve is in a reciprocal relationship with that of a digital camera, to illuminate a to-be-measured object, and sequentially obtains multispectral images of the to-be-measured object that are acquired by the digital camera; extracts color information of a surface of the to-be-measured object from the multispectral images; and reconstructs spectral reflectivity of the surface of the to-be-measured object, to measure a color of the to-be-measured object. The method has advantages, such as a simple algorithm, a small system error, high measurement accuracy, and can break through limitations of conventional color measurement methods. Non-contact color measurement can be used in fields in which conventional color measurement instruments cannot be applied. 2. In the present invention, an LED lamp is used as an active lighting source to construct a multispectral imaging system, so as to avoid use of an optical splitting system, reduce system costs, and increase a multispectral image acquisition speed.

A person of ordinary skill in the art may understand that all or some of the steps of the method embodiments may be implemented by a program instructing relevant hardware.

The foregoing embodiments are preferred implementations of the present invention, but the implementations of the present invention are not limited to the foregoing embodiments. Any variation, modification, replacement, combination, or simplification made without departing from the spirit and principle of the present invention is regarded as an equivalent replacement manner and shall fall within the protection scope of the present invention.

What is claimed is:

1. An LED lighting based multispectral imaging system for color measurement, comprising:
   a main control computer; and
   an enclosed type lamp box for placing a to-be-measured object,
   wherein a digital camera is provided at the top of the lamp box, an LED lamp set control apparatus is provided in central enclosed space at the bottom of the lamp box, a drawer type bearing platform that is used for placing the to-be-measured object and that enters or exits from the lamp box through an external drive is provided in an upper part of the lamp box, and at least one LED lamp set is provided on each of two sides at the bottom of the lamp box;
   the digital camera aims at the to-be-measured object and is connected to the main control computer and is configured to shoot an image of the to-be-measured object;
   all LED lamp sets have a same structure;
   each LED lamp set comprises a plurality of monochromatic LED lamps with different peak wavelengths;
   the LED lamp set control apparatus is connected to each LED lamp set and the main control computer and is configured to receive a control instruction sent by the main control computer and control turn-on or turn-off and an illumination degree/illumination degrees of one or more LED lamps of the LED lamp set according to the received control instruction; and
   the main control computer is configured to control, according to a spectral sensitivity curve of the digital camera, spectral power distribution of each LED lamp set to be in a reciprocal relationship with the spectral sensitivity curve of the digital camera, output the control instruction to drive the LED lamp set control apparatus to turn on a corresponding LED lamp in each LED lamp set, receive an image, of the to-be-measured object, that is shot by the digital camera when the corresponding LED lamp in the LED lamp set is turned on, and extract a camera response and perform calculation, to obtain spectral reflectivity of each pixel of the to-be-measured object.

2. The LED lighting based multispectral imaging system for color measurement according to claim 1, wherein all monochromatic LED lamps comprised in any LED lamp set are cross arranged on an LED circuit board provided with an LED lamp bead array, the LED circuit board is fastened onto a radiating fin, and a light scattering sheet is provided at a specific distance from one side of a luminous surface of the LED circuit board.

3. The LED lighting based multispectral imaging system for color measurement according to claim 2, wherein any LED lamp set is fastened onto two sides at the bottom of the lamp box, and forms a specific acute angle with a plane of the bottom of the lamp box; and the luminous surface of LED lamp set tilts towards one of inner walls on two sides of the lamp box.

4. The LED lighting based multispectral imaging system for color measurement according to claim 3, wherein there are at least two LED lamp sets having an exactly same structure, and the at least two LED lamp sets are provided opposite to each other on two sides of the to-be-measured object.

5. The LED lighting based multispectral imaging system for color measurement according to claim 1, wherein the digital camera is at least one of a black-and-white camera and a color camera.

6. The LED lighting based multispectral imaging system for color measurement according to claim 2, wherein the digital camera is at least one of a black-and-white camera and a color camera.

7. The LED lighting based multispectral imaging system for color measurement according to claim 3, wherein the digital camera is at least one of a black-and-white camera and a color camera.

8. The LED lighting based multispectral imaging system for color measurement according to claim 4, wherein the digital camera is at least one of a black-and-white camera and a color camera.

* * * * *